United States Patent
Lansalot-Matras et al.

(10) Patent No.: US 10,174,423 B2
(45) Date of Patent: Jan. 8, 2019

(54) NIOBIUM-CONTAINING FILM FORMING COMPOSITIONS AND VAPOR DEPOSITION OF NIOBIUM-CONTAINING FILMS

(71) Applicant: L'Air Liquide, Société Anonyme pour l'Etude et l'Exploitation des Procédés Georges Claude, Paris (FR)

(72) Inventors: Clément Lansalot-Matras, Princeton, NJ (US); Jooho Lee, Seoul (KR); Wontae Noh, Seoul (KR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 15/636,354

(22) Filed: Jun. 28, 2017

(65) Prior Publication Data

US 2017/0298511 A1  Oct. 19, 2017

(51) Int. Cl.
| | |
|---|---|
| *C23C 16/455* | (2006.01) |
| *C09D 1/00* | (2006.01) |
| *C09D 5/00* | (2006.01) |
| *C01B 21/06* | (2006.01) |
| *C07F 9/00* | (2006.01) |

(52) U.S. Cl.
CPC .... *C23C 16/45553* (2013.01); *C01B 21/0617* (2013.01); *C07F 9/00* (2013.01); *C09D 1/00* (2013.01); *C09D 5/00* (2013.01); *C01P 2006/40* (2013.01)

(58) Field of Classification Search
CPC .............................................. C23C 16/45525
See application file for complete search history.

(56) References Cited

U.S. PATENT DOCUMENTS

| | | | |
|---|---|---|---|
| 2006/0040480 A1* | 2/2006 | Derderian | C23C 16/405 438/584 |
| 2008/0241575 A1 | 10/2008 | Lavoie et al. | |
| 2017/0152277 A1 | 6/2017 | Lim et al. | |

FOREIGN PATENT DOCUMENTS

| | | |
|---|---|---|
| EP | 2 573 094 | 3/2013 |
| KR | 10 2017 0063092 | 6/2017 |
| WO | WO 2010 040741 | 4/2010 |

OTHER PUBLICATIONS

Alén, P. et al., "The growth and diffusion barrier properties of atomic layer deposited NbNx thin films," Thin Solid Films 491 (2005) 235-241.

Elers, K.-E. et al., "NbCl$_5$ as a precursor in atomic layer epitaxy," Applied Surface Science 82/83 (1994) 468-474.

Gilmore, C.M. et al., "Stabilized zirconia-alumina thin films," J. Vac. Sci. Technol A 4 (6) 1986 2598-2600.

Gordon, R.G., "Atomic layer deposition (ALD): an enabler for nanoscience and nanotechnology," downloaded from https://www.scribd.com/document/310950017/ALD-an-Enabler-for-Nanoscience-and-Nanotechnology-Gordon-Harvard-Revied-Amide-Compounds on Nov. 18, 2016.

(Continued)

*Primary Examiner* — Joseph A Miller, Jr.
(74) *Attorney, Agent, or Firm* — Patricia E. McQueeney

(57) ABSTRACT

Disclosed are Niobium-containing film forming compositions, methods of synthesizing the same, and methods of forming Niobium-containing films on one or more substrates via atomic layer deposition processes using the Niobium-containing film forming compositions.

6 Claims, 8 Drawing Sheets

(56) References Cited

OTHER PUBLICATIONS

Gust, K.R. et al., "Synthesis, structure, and properties of niobium and tantalum imido complexes bearing pyrazolato ligands. Crystal structures of Ta(Nt—Bu)(t—Bu$_2$Pz)$_3$, Ta(Ni—Pr)(t—Bu$_2$Pz)$_3$, Ta(Nt—Bu)(Me$_2$Pz)$_3$(Py), and Ta(Nt—Bu)(t-Bu$_2$Pz)$_2$(Cl)(Py)," Polyhedron 20 (2001) 805-813.

Kittl, J.A. et al., "High-k dielectrics for future generation memory devices," Microelectronic Engineering 86 (2009) 1789-1795.

Ritala, M. et al., "Effects of intermediate zinc pulses on properties of TiN and NbN films deposited by atomic layer epitaxy," Applied Surface Science 120 (1997) 199-212.

Romestain, R. et al., "Fabrication of a superconducting niobium nitride hot electron bolometer for single-photon counting," New Journal of Physics 6 (2004) 129 1-15.

Dezelah, C.L. et al., "A pyrazolate-based metalorganic tantalum precursors that exhibits high thermal stability and its use in the atomic layer deposition of Ta$_2$O$_5$," J. Am. Chem. Soc., vol. 129, No. 41, 2007, 12370-12371.

International Search Report and Written Opinion for corresponding PCT/US2018/036015, dated Sep. 21, 2018.

\* cited by examiner

NIOBIUM-CONTAINING FILM FORMING COMPOSITIONS AND VAPOR DEPOSITION OF NIOBIUM-CONTAINING FILMS

TECHNICAL FIELD

Disclosed are Niobium-containing film forming compositions, methods of synthesizing the same, and methods of forming Niobium-containing films on one or more substrates via vapor deposition processes using the Niobium-containing film forming compositions.

BACKGROUND

Traditionally, thin films of Zirconium Oxide ($ZrO_2$) have been used as high-k materials for insulating layers in capacitor structures. Recently, Niobium Oxide ($Nb_2O_5$) thin films sandwiched between two $ZrO_2$ dielectric layers have been found to help significantly reduce leakage current and stabilize the cubic/tetragonal phase of the $ZrO_2$. The resulting $ZrO_2/Nb_2O_5/ZrO_2$ stack provides higher k values in the current Metal-Insulator-Metal (MIM) capacitor of Dynamic Random Access Memory (DRAM). (Alumina, J. Vac. Sci. Techno A 4 (6), 1986 and Microelectronic Engineering 88 (2009)1789-1795).

Metal Nitride films, such as Niobium Nitride ($NbN_x$ wherein x is approximately 1) have been used for some niche applications, such as photodetectors at extremely low T (4K) where they become superconductors. Romestain et al., New Journal of Physics, Vol. 6, 2004. During the past decade, metal nitrides such as TiN, TaN, WN or NbN have increasingly been used as diffusion barrier and adhesion/glue layers in microelectronic devices [Applied Surface Science 120 (1997) 199-212]. $NbCl_5$ for instance has been examined as a niobium source for Atomic Layer Epitaxial growth of $NbN_x$, but the process required Zn as a reducing agent [Applied Surface Science 82/83 (1994) 468-474], $NbN_x$ films were also deposited by atomic layer deposition using $NbCl_5$ and $NH_3$, [Thin Solid Films 491 (2005) 235-241]. The chlorine content showed strong temperature dependence: the film deposited at 500° C. was almost chlorine free while the chlorine content was 8 at. % when the deposition temperature was as low as 250° C. Id. The 500° C. chlorine free deposition temperature may be too high for production of some semiconductor devices. The high melting point of $NbCl_5$ also makes this precursor difficult to use in the vapor deposition process.

Gust et al. disclose the synthesis, structure, and properties of niobium and tantalum imido complexes bearing pyrazolato ligands and their potential use for the growth of tantalum nitride films by CVD. Polyhedron 20 (2001) 805-813. However, one of ordinary skill in the art will recognize that not ail CVD precursors may be suitable for ALD processes. See, e.g., Gordon et al. at https://www.scribd.com/document/310950017/ALD-an-Enabler-for-Nanoscience-and-Nanotechnology-Gordon-Harvard-Revied-Amide-Compounds.

A need remains for developing novel, liquid or low melting point (<50° C), highly thermally stable, Niobium-containing precursor molecules suitable for Atomic Layer Deposition of Nb containing films, whether insulating or conductive.

Notation and Nomenclature

Certain abbreviations, symbols, and terms are used throughout the following description and claims, and include:

As used herein, the indefinite article "a" or "an" means one or more.

As used herein, the terms "approximately" or "about" mean±10% of the value stated.

Any and all ranges recited herein are inclusive of their endpoints (i.e., x=1to 4 or x ranges from 1 to 4 includes x=1, x=4, and x=any number in between), irrespective of whether the term "inclusively" is used.

The standard abbreviations of the elements from the periodic table of elements are used herein. It should be understood that elements may be referred to by these abbreviations (e.g., Nb refers to Niobium, N refers to nitrogen, C refers to carbon, etc.).

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x (NR^2R^3)_{(4-x)}$, where x is 2 or 3, the two or three $R^1$ groups may, but need not be identical to each other or to $R^2$ or to $R^3$.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation "Me" refers to a methyl group; the abbreviation "Et" refers to an ethyl group; the abbreviation "Pr" refers to a propyl group; the abbreviation "nPr" refers to a "normal" or linear propyl group; the abbreviation "iPt" refers to an isopropyl group; the abbreviation "Bu" refers to a butyl group; the abbreviation "nBu" refers to a "normal" or linear butyl group; the abbreviation "tBu" refers to a tert-butyl group, also known as 1,1-dimethylethyl; the abbreviation "sBu" refers to a sec-butyl group, also known as 1-methylpropyl; the abbreviation "iBu" refers to an iso-butyl group, also known as 2-methylpropyl; the abbreviation "amyl" refers to an amyl or pentyl group; the abbreviation "tAmyl" refers to a tert-amyl group, also known as 1,1-dimethylpropyl.

As used herein, the abbreviation "IMS" refers to trimethylsilyl ($Me_3Si$—); the abbreviation "DMS" refers to dimethylsilyl ($Me_2HSi$—); the abbreviation "MMS" refers to monomethylsilyl ($MeH_2Si$—); the abbreviation "py" refers to pyridine; and the abbreviation $R^1,R^2,R^3$-Pyr refers to a pyrazolyl ligand having the following structure:

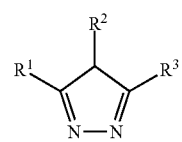

Please note that the films or layers deposited, such as niobium oxide or niobium nitride, may be listed throughout the specification and claims without reference to their proper stoichiometry (e.g., $NbO=Nb_2O_5$). These layers may also contain Hydrogen, typically from 0 at % to 15 at %.

However, since not routinely measured, any film compositions given ignore their H content, unless explicitly stated otherwise.

SUMMARY

Disclosed are Niobium-containing film forming compositions comprising a precursor having the formula:

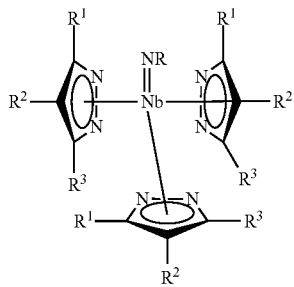

wherein each R, $R^1$, $R^2$, and $R^3$ is independently H, an alkyl group, or $R'_3Si$, with each R' independently being H or an alkyl group. The disclosed Niobium-containing film forming compositions may include one or more of the following aspects:
- each R $R^1$, $R^2$ and $R^3$ independently being selected from H, Me, Et, nPr, iPr, tBu, sBu, iBu, nBu, tAmyl, $SiMe_3$, $SiMe_2H$, or $SiH_2Me$;
- each R being iPr, tBu or tAmyl;
- each $R^2$ being H or Me;
- R, $R^1$, $R^2$ and $R^3$ being respectively tBu, H, H and H;
- R, $R^1$, $R^2$ and $R^3$ being respectively tBu, Me, H and H;
- R, $R^1$, $R^2$ and $R^3$ being respectively tBu, Me, H and Me;
- R, $R^1$, $R^2$ and $R^3$ being respectively tBu, Me, Me and Me;
- R, $R^1$, $R^2$ and $R^3$ being respectively tBu, Et, H and Et;
- R, $R^1$, $R^2$ and $R^3$ being respectively tBu, nPr, H and nPr;
- R, $R^1$, $R^2$ and $R^3$ being respectively tBu, iPr, H and iPr;
- R, $R^1$, $R^2$ and $R^3$ being respectively tBu, tBu, H and tBu;
- R, $R^1$, $R^2$ and $R^3$ being respectively tBu, tAmyl, H and tAmyl;
- R, $R^1$, $R^2$ and $R^3$ being respectively tBu, iPr, H and tBu;
- R, $R^1$, $R^2$ and $R^3$ being respectively tBu, iPr, H and Me;
- R, $R^1$, $R^2$ and $R^3$ being respectively tBu, iPr, H and Et;
- R, $R^1$, $R^2$ and $R^3$ being respectively tBu, $SiMe_3$, H and $SiMe_3$;
- R, $R^1$, $R^2$ and $R^3$ being respectively tBu, $SiHMe_2$, H and $SiHMe_2$;
- R, $R^1$, $R^2$ and $R^3$ being respectively tBu, $SiH_2Me$, H and $SiH_2Me$;
- R, $R^1$, $R^2$ and $R^3$ being respectively tAmyl, H, H and H;
- R, $R^1$, $R^2$ and $R^3$ being respectively tAmyl, Me, H and H;
- R, $R^1$, $R^2$ and $R^3$ being respectively tAmyl, Me, H and Me;
- R, $R^1$, $R^2$ and $R^3$ being respectively tAmyl, Me, Me and Me;
- R, $R^1$, $R^2$ and $R^3$ being respectively tAmyl, Et, H and Et;
- R, $R^1$, $R^2$ and $R^3$ being respectively tAmyl, nPr, H and nPr;
- R, $R^1$, $R^2$ and $R^3$ being respectively tAmyl, iPr, H and iPr;
- R, $R^1$, $R^2$ and $R^3$ being respectively tAmyl, tBu, H and tBu;
- R, $R^1$, $R^2$ and $R^3$ being respectively tAmyl, tAmyl, H and tAmyl;
- R, $R^1$, $R^2$ and $R^3$ being respectively tAmyl, iPr, H and tBu;
- R, $R^1$, $R^2$ and $R^3$ being respectively tAmyl, iPr, H and Me;
- R, $R^1$, $R^2$ and $R^3$ being respectively tAmyl, iPr, H and Et;
- R, $R^1$, $R^2$ and $R^3$ being respectively tAmyl, $SiMe_3$, H and $SiMe_3$;
- R, $R^1$, $R^2$ and $R^3$ being respectively tAmyl, $SiHMe_2$, H and $SiHMe_2$;
- R, $R^1$, $R^2$ and $R^3$ being respectively tAmyl, $SiH_2Me$, H and $SiH_2Me$;
- R, $R^1$, $R^2$ and $R^3$ being respectively iPr, H, H and H;
- R, $R^1$, $R^2$ and $R^3$ being respectively iPr, Me, H and H;
- R, $R^1$, $R^2$ and $R^3$ being respectively iPr, Me, H and Me;
- R, $R^1$, $R^2$ and $R^3$ being respectively iPr, Me, Me and Me;
- R, $R^1$, $R^2$ and $R^3$ being respectively iPr, Et, H and Et;
- R, $R^1$, $R^2$ and $R^3$ being respectively iPr, nPr, H and nPr;
- R, $R^1$, $R^2$ and $R^3$ being respectively iPr, iPr, H and iPr;
- R, $R^1$, $R^2$ and $R^3$ being respectively iPr, tBu, H and tBu;
- R, $R^1$, $R^2$ and $R^3$ being respectively iPr, tAmyl, H and tAmyl;
- R, $R^1$, $R^2$ and $R^3$ being respectively iPr, iPr, H and tBu;
- R, $R^1$, $R^2$ and $R^3$ being respectively iPr, iPr, H and Me;
- R, $R^1$, $R^2$ and $R^3$ being respectively iPr, iPr, H and Et;
- R, $R^1$, $R^2$ and $R^3$ being respectively iPr, $SiMe_3$, H and $SiMe_3$;
- R, $R^1$, $R^2$ and $R^3$ being respectively iPr, $SiHMe_2$, H and $SiHMe_2$;
- R, $R^1$, $R^2$ and $R^3$ being respectively iPr, $SiH_2Me$, H and $SiH_2Me$;
- the precursor having the formula Nb(=NiPr)(H,H,H-Pyr)$_3$;
- the precursor having the formula Nb(=NiPr)(Me,H,H-Pyr)$_3$;
- the precursor having the formula Nb(=NiPr)(Me,H,Me-Pyr)$_3$;
- the precursor having the formula Nb(=NiPr)(Me,Me,Me-Pyr)$_3$;
- the precursor having the formula Nb(=NiPr)(EtiH1Et-Pyr)$_3$;
- the precursor having the formula Nb(=NiPr)(nPr,H,nPr-Pyr)$_3$;
- the precursor having the formula Nb(=NiPr)(iPr,HjPr-Pyr)$_3$;
- the precursor having the formula Nb(=NiPr)(tBu,H,tBu-Pyr)$_3$;
- the precursor having the formula Nb(=NiPr)(iBu,H,iBu-Pyr)$_3$;
- the precursor having the formula Nb(=NiPr)(nBu,H,nBu-Pyr)$_3$;
- the precursor having the formula Nb(=NiPr)(sBu,H,sBu-Pyr)$_3$;
- the precursor having the formula Nb(=NiPr)(tAmyl,H,tAmyl-Pyr)$_3$;
- the precursor having the formula Nb(=NiPr)(iPr,H,tBu-Pyr)$_3$;
- the precursor having the formula Nb(=NiPr)(iPr,H,Me-Pyr)$_3$;
- the precursor having the formula Nb(=NiPr)(iPr,H,Et-Pyr)$_3$;
- the precursor having the formula Nb(=NiPr)(TMS,H,TMS-Pyr)$_3$;
- the precursor having the formula Nb(=NiPr)(DMS,H,DMS-Pyr)$_3$;
- The precursor having the formula Nb(=NiPr)(MMS,H,MMS-Pyr)$_3$;
- the precursor having the formula Nb(=NtBu)(H,H,H-Pyr)$_3$;
- the precursor having the formula Nb(=NtBu)(Me,H,H-Pyr)$_3$;

the precursor having the formula Nb(=NtBu)(Me,H,Me-Pyr)₃;
the precursor having the formula Nb(=NtBu)(Me,Me,Me-Pyr)₃;
the precursor having the formula Nb(=NtBu)(Et,H,Et-Pyr)₃;
the precursor having the formula Nb(=NtBu)(nPr,H,nPr-Pyr)₃;
the precursor having the formula Nb(=NtBu)(iPr,H,iPr-Pyr)₃;
the precursor having the formula Nb(=NtBu)(tBu,H,tBu-Pyr)₃;
the precursor having the formula Nb(=NtBu)(sBu,H,sBu-Pyr)₃;
the precursor having the formula Nb(=NtBu)(nBu,H,nBu-Pyr)₃;
the precursor having the formula Nb(=NtBu)(iBu,H,iBu-Pyr)₃;
the precursor having the formula Nb(=NtBu)(tAmyl,H,tAmyl-Pyr)₃;
the precursor having the formula Nb(=:NtBu)(iPr,H,tBu-Pyr)₃;
the precursor having the formula Nb(=NtBu)(iPr,H,Me-Pyr)₃;
the precursor having the formula Nb(=NtBu)(iPr,H,Et-Pyr)₃;
the precursor having the formula Nb(=NtBu)(TMS,H,TM-Pyr)₃;
the precursor having the formula Nb(=NtBu)(DMS,H,DMS-Pyr)₃;
the precursor having the formula Nb(=NtBu)(MMS,H,MMS-Pyr)₃;
the precursor having the formula Nb(=NtAmyl)(H,H,H-Pyr)₃;
the precursor having the formula Nb(=NtAmyl)(Me,H,H-Pyr)₃;
the precursor having the formula Nb(=NtAmyl)(Me,H,Me-Pyr)₃;
the precursor having the formula Nb(=NtAmyl)(Me,Me,Me-Pyr)₃;
the precursor having the formula Nb(=NtAmyl)(Et,H,Et-Pyr)₃;
the precursor having the formula Nb(=NtAmyl)(nPr,H,nPr-Pyr)₃;
the precursor having the formula Nb(=NtAmyl)(iPr,H,iPr-Pyr)₃;
the precursor having the formula Nb(=NtAmyl)(tBu,H,tBu-Pyr)₃;
the precursor having the formula Nb(=NtAmyl)(sBu,H,sBu-Pyr)₃;
the precursor having the formula Nb(=NtAmyl)(nBu,H,nBu-Pyr)₃;
the precursor having the formula Nb(=NtAmyl)(iBu,H,iBu-Pyr)₃;
the precursor having the formula Nb(=NtAmyl)(tAmyl,H,tAmyl-Pyr)₃;
the precursor having the formula Nb(=NtAmyl)(iPr,H,tBu-Pyr)₃;
the precursor having the formula Nb(=NtAmyl)(iPr,H,Me-Pyr)₃;
the precursor having the formula Nb(=NtAmyl)(iPr,H,Et-Pyr)₃;
the precursor having the formula Nb(=NtAmyl)(TMS,H,TMS-Pyr)₃;
the precursor having the formula Nb(=NtAmyl)(DMS,H,DMS-Pyr)₃;
the precursor having the formula Nb(=NtAmyl)(MMS,H,MMS-Pyr)₃;
the Niobium-containing film forming composition comprising between approximately 95.0% w/w and approximately 100.0% w/w of the precursor;
the Niobium-containing film forming composition comprising between approximately 0.0% w/w and approximately 5.0% w/w impurities;
the Niobium-containing film forming composition comprising between approximately 0.0% w/w and approximately 2.0% w/w impurities:
the Niobium-containing film forming composition comprising between approximately 0.0% w/w and approximately 1.0% w/w impurities;
the impurities including pyrazoles; pyridines; alkylamines; alkylimines; THF; ether; pentane; cyclohexane; heptanes; benzene; toluene; chlorinated metal compounds; lithium, sodium, or potassium pyrazole;
the Niobium-containing film forming composition comprising between approximately 0.0% w/w and approximately 2.0% w/w pyrazoles impurities;
the Niobium-containing film forming composition comprising between approximately 0.0% w/w and approximately 2.0% w/w pyridines impurities;
the Niobium-containing film forming composition comprising between approximately 0.0% w/w and approximately 2.0% w/w alkylamine impurities;
the Niobium-containing film forming composition comprising between approximately 0.0% w/w and approximately 2.0% w/w alkylimine impurities;
the Niobium-containing film forming composition comprising between approximately 0.0% w/w and approximately 2.0% w/w THF impurities;
the Niobium-containing film forming composition comprising between approximately 0.0% w/w and approximately 2.0% w/w ether impurities;
the Niobium-containing film forming composition comprising between approximately 0.0% w/w and approximately 2.0% w/w pentane impurities;
the Niobium-containing film forming composition comprising between approximately 0.0% w/w and approximately 2.0% w/w cyclohexane impurities;
the Niobium-containing film forming composition comprising between approximately 0.0% w/w and approximately 2.0% w/w heptanes impurities;
the Niobium-containing film forming composition comprising between approximately 0.0% w/w and approximately 2.0% w/w benzene impurities;
the Niobium-containing film forming composition comprising between approximately 0.0% w/w and approximately 2.0% w/w toluene impurities;
the Niobium-containing film forming composition comprising between approximately 0.0% w/w and approximately 2.0% w/w chlorinated metal compound impurities;
the Niobium-containing film forming composition comprising between approximately 0.0% w/w and approximately 2.0% w/w lithum, sodium, or potassium pyrazolyl impurities;
the Niobium-containing film forming composition comprising between approximately 0 ppbw and approximately 1 ppmw metal impurities;
the Niobium-containing film forming composition comprising between approximately 0 ppbw and approximately 500 ppbw metal impurities;
the metal impurities including Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), and Zinc (Zn);

the Niobium-containing film forming composition comprising between approximately 0 ppbw and approximately 500 ppbw Al impurities;

the Niobium-containing film forming composition comprising between approximately 0 ppbw and approximately 500 ppbw As impurities;

the Niobium-containing film forming composition comprising between approximately 0 ppbw and approximately 500 ppbw Ba impurities;

the Niobium-containing film forming composition comprising between approximately 0 ppbw and approximately 500 ppbw Be impurities;

the Niobium-containing film forming composition comprising between approximately 0 ppbw and approximately 500 ppbw Bi impurities;

the Niobium-containing film forming composition comprising between approximately 0 ppbw and approximately 500 ppbw Cd impurities;

the Niobium-containing film forming composition comprising between approximately 0 ppbw and approximately 500 ppbw Ca impurities;

the Niobium-containing film forming composition comprising between approximately 0 ppbw and approximately 500 ppbw Cr impurities;

the Niobium-containing film forming composition comprising between approximately 0 ppbw and approximately 500 ppbw Co impurities;

the Niobium-containing film forming composition comprising between approximately 0 ppbw and approximately 500 ppbw Cu impurities;

the Niobium-containing film forming composition comprising between approximately 0 ppbw and approximately 500 ppbw Ga impurities;

the Niobium-containing film forming composition comprising between approximately 0 ppbw and approximately 500 ppbw Ge impurities;

the Niobium-containing film forming composition comprising between approximately 0 ppbw and approximately 500 ppbw Hf impurities;

the Niobium-containing film forming composition comprising between approximately 0 ppbw and approximately 500 ppbw Zr impurities;

the Niobium-containing film forming composition comprising between approximately 0 ppbw and approximately 500 ppbw In impurities;

the Niobium-containing film forming composition comprising between approximately 0 ppbw and approximately 500 ppbw Fe impurities;

the Niobium-containing film forming composition comprising between approximately 0 ppbw and approximately 500 ppbw Pb impurities;

the Niobium-containing film forming composition comprising between approximately 0 ppbw and approximately 500 ppbw Li impurities;

the Niobium-containing film forming composition comprising between approximately 0 ppbw and approximately 500 ppbw Mg impurities;

the Niobium-containing film forming composition comprising between approximately 0 ppbw and approximately 500 ppbw Mn impurities;

the Niobium-containing film forming composition comprising between approximately 0 ppbw and approximately 500 ppbw W impurities;

the Niobium-containing film forming composition comprising between approximately 0 ppbw and approximately 500 ppbw Ni impurities;

the Niobium-containing film forming composition comprising between approximately 0 ppbw and approximately 500 ppbw K impurities;

the Niobium-containing film forming composition comprising between approximately 0 ppbw and approximately 500 ppbw Na impurities;

the Niobium-containing film forming composition comprising between approximately 0 ppbw and approximately 500 ppbw Sr impurities;

the Niobium-containing film forming composition comprising between approximately 0 ppbw and approximately 500 ppbw Th impurities;

the Niobium-containing film forming composition comprising between approximately 0 ppbw and approximately 500 ppbw Sn impurities;

the Niobium-containing film forming composition comprising between approximately 0 ppbw and approximately 500 ppbw Ti impurities;

the Niobium-containing film forming composition comprising between approximately 0 ppbw and approximately 500 ppbw U impurities; and the Niobium-containing film forming composition comprising between approximately 0 ppbw and approximately 500 ppbw Zn impurities.

Also disclosed are processes for the deposition of Niobium-containing films on substrates. The Niobium-containing film forming composition(s) disclosed above is introduced into a reactor having a substrate disposed therein. At least part of the precursor is deposited onto the substrate to form the Niobium-containing layer. The disclosed processes may further include one or more of the following aspects:

introducing a reactant into the reactor;

the reactant being plasma-treated;

the reactant not being plasma-treated;

the reactant being remote plasma-treated;

the reactant being selected from the group consisting of $H_2$, $H_2CO$, $N_2H_4$, $NH_3$, hydrogen radicals, a primary amine, a secondary amine, a tertiary amine, trisilylamine, and mixtures thereof;

the reactant being $H_2$;

the reactant being $NH_3$;

the reactant being selected from the group consisting of: $O_2$, $O_3$, $H_2O$, $H_2O_2$, NO, $N_2O$, $NO_2$, oxygen radicals thereof, and mixtures thereof;

the reactant being $H_2O$;

the reactant being plasma treated $O_2$;

the reactant being $O_3$;

the Niobium-containing precursor and the reactant being introduced into the chamber sequentially;

the introduction of the Niobium containing precursor and the introduction of the reactant being temporally or spatially separated by an inert gas purge to avoid the gas phase mixing of the reactant and the Nb containing precursor;

introducing another precursor into the reactor;

the second precursor comprising an element M selected from a Group IV element, another Group V element, Si, Ge, Al, or any Lanthanide;

the Niobium-containing film and the second precursor forming a laminate;

the Niobium-containing film and the second precursor forming a NbO/MO laminate;
the reactor being configured for atomic layer deposition;
the reactor being configured for plasma enhanced atomic layer deposition;
the reactor being configured for spatial atomic layer deposition;
the Niobium containing film being $Nb_nO_m$, wherein each of n and m is an integer which inclusively range from 1 to 6;
the Niobium containing film being $NbO_2$ or $Nb_2O_5$;
the Niobium containing film being $Nb_oN_p$, wherein each of o and p is an integer which inclusively range from 1 to 6;
the Niobium containing film being NbN;
the Niobium containing film being $Nb_oN_pO_q$, wherein each of o, p and q is an integer which inclusively range from 1 to 8;
the Niobium containing film being NbON;
the Niobium containing film being NbMO, wherein M is a Group IV element, a different Group V element, Si, Ge, Al, or any Lanthanide.

BRIEF DESCRITPION OF THE FIGURES

For a further understanding of the nature and objects of the present invention, reference should be made to the following detailed description, taken in conjunction with the accompanying FIG. wherein.

DESCRIPTION OF PREFERRED EMBODIMENTS

Figure 1:
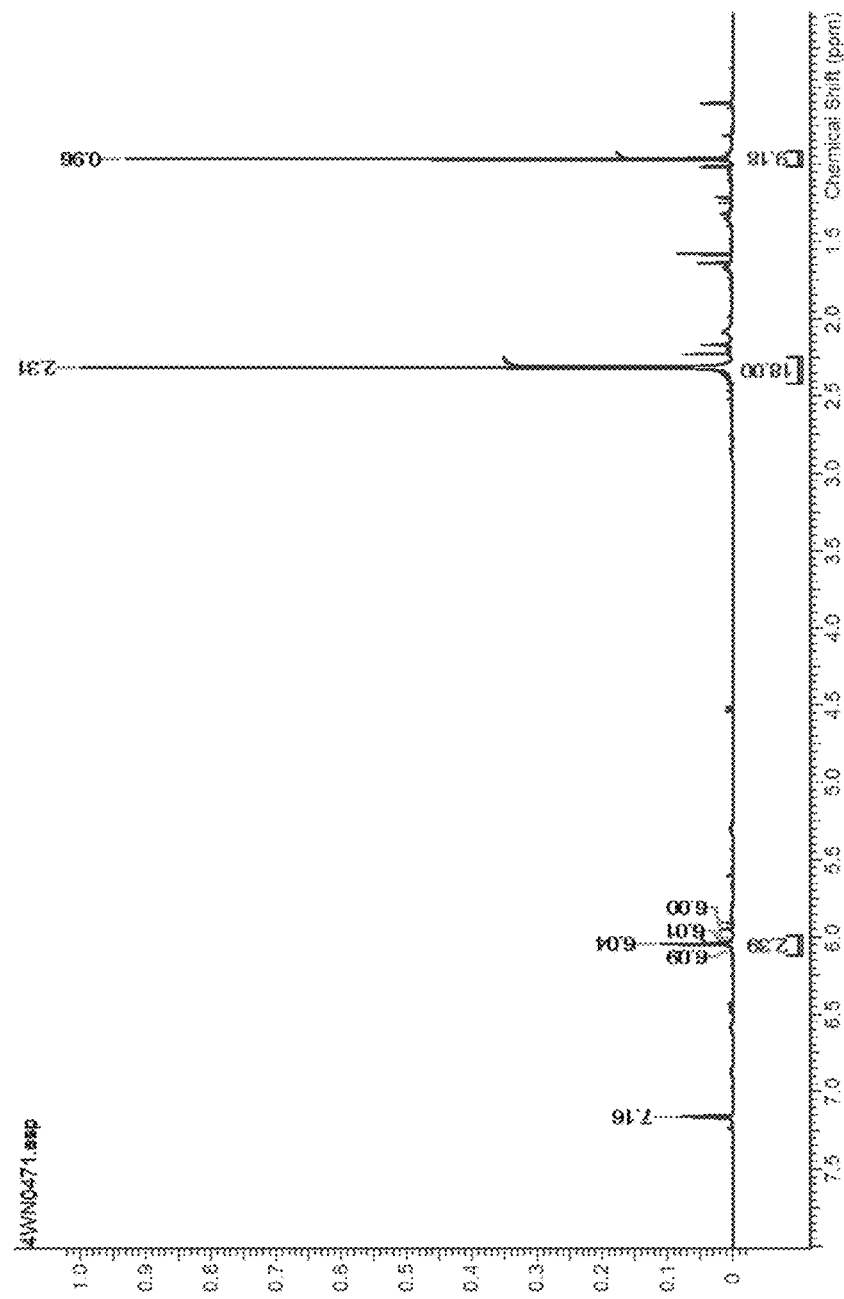
FIG. 1 is a $^1$HNMR spectrum of Niobium (tButylimido) tris(3,5-dimethylpyrazolyl) [Nb(=NtBu)(Me,H,Me-Pyr)$_3$]

Disclosed are Niobium-containing film forming compositions comprising precursors having the formula:

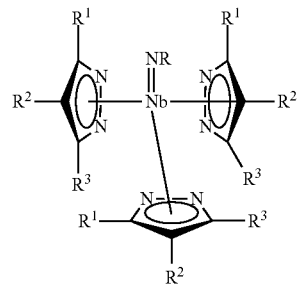

wherein each R, $R^1$, $R^2$, and $R^3$ is independently H, an alkyl group, or R'$_3$Si, with each R' independently being H or an alkyl group. As illustrated in the formula, the nitrogen atoms may be bonded to the niobium atom, resulting in a tetracoordinate Nb(V) center. The resulting geometry may be tetrahedral where the center of the nitrogen-nitrogen bond in each 3,5-dialkylpyrazolyl moiety is considered as a monodentate ligand. The carbon atoms in the pyrazolyl ligand may be sp$^2$hybridized, resulting in a delocalized charge across the monoanionic ligand where Nb can be considered to be coordinated by a η5-bonded pyrazolato ring. In this embodiment, the formula would be:

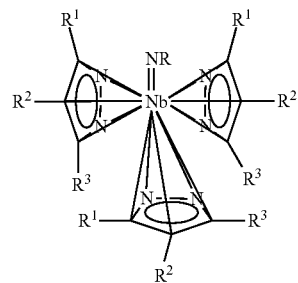

Alternatively, the carbon atoms in the pyrazolyl ligand may be either sp3hybridized or some combination of sp2 and sp3 hybridized, resulting in a negative charge on one of the nitrogen atoms and resulting in a neutral charge on the other of the nitrogen atoms. In this embodiment, the formula would be

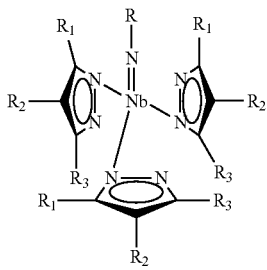

For convenience, the delocalized bonds are depicted in the formulae below. However, each formula may alternatively be represented by this formula showing a single bond between N and Nb, When R=iPr, the Niobium-containing film forming precursor may have the formula Nb(=NiPr)(R$^1$,R$^2$,R$^3$-Pyr)$_3$:

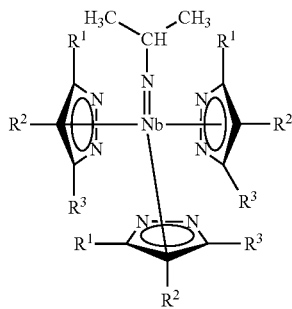

wherein each $R^1$, $R^2$, and $R^3$ is independently H, an alkyl group, or $SiR'_3$, with each R' independently being H or an alkyl group. Preferably, each $R^1$, $R^2$, and $R^3$ is independently H, Me, Et, nPr, iPr, tBu, sBu, iBu, nBu, tAmyl, $SiMe_3$, $SiMe_2H$, or $SiH_2Me$.

Exemplary precursors include Nb(=NiPr)(H,H,H-Pyr)$_3$, Nb(=NiPr)(Me,H,H-Pyr)$_3$, Nb(=NiPr)(Me,H,Me-Pyr)$_3$, Nb(=NiPr)(Me,Me,Me-Pyr)$_3$, Nb(=NiPr)(Et,H,Et-Pyr)$_3$, Nb(=NiPr)(nPr,H,nPr-Pyr)$_3$, Nb(=NiPr)(iPr,H,iPr-Pyr)$_3$, Nb(=NiPr)(tBu,H,tBu-Pyr)$_3$, Nb(=NiPr)(iBu,H,iBu-Pyr)$_3$, Nb(=NiPr)(nBu,H,nBu-Pyr)$_3$, Nb(=NiPr)(sBu,H,sBu-Pyr)$_3$, Nb(=NiPr)(tAmyl,H,tAmyl-Pyr)$_3$, Nb(=NiPr)(iPr,H,tBu-Pyr)$_3$, Nb(=NiPr)(iPr,H,Me-Pyr)$_3$, Nb(=NiPr)(iPr,H,Et-Pyr)$_3$, Nb(=NiPr)(TMS,H,TMS-Pyr)$_3$, Nb(=NiPr)(DMS,H,DMS-Pyr)$_3$, or Nb(=NiPr)(MMS,H,MMS-Pyr)$_3$.

When R=tBu, the Niobium-containing film forming precursor may have the formula Nb(=NtBu)($R^1$,$R^2$,$R^3$-Pyr)$_3$:

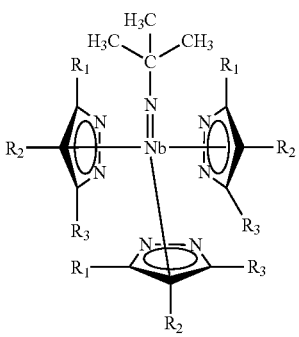

wherein each $R^1$, $R^2$, and $R^3$ is independently H, an alkyl group, or $SiR'_3$, with each R' independently being H or an alkyl group. Preferably, each $R^1$, $R^2$, and $R^3$ is independently H, Me, Et, nPr, iPr, tBu, sBu, iBu, nBu, tAmyl, $SiMe_3$, $SiMe_2H$, or $SiH_2Me$.

Exemplary precursors include Nb(=NtBu)(H,H,H-Pyr)$_3$, Nb(=NtBu)(Me,H,H-Pyr)$_3$, Nb(=NtBu)(Me,H,Me-Pyr)$_3$, Nb(=NtBu)(Me,Me,Me-Pyr)$_3$, Nb(=NtBu)(Et,H,Et-Pyr)$_3$, Nb(=NtBu)(nPr,H,nPr-Pyr)$_3$, Nb(=NtBu)(iPr,H,iPr-Pyr)$_3$, Nb(=NtBu)(tBu,H,tBu-Pyr)$_3$, Nb(=NtBu)(sBu,H,sBu-Pyr)$_3$, Nb(=NtBu)(nBu,H,nBu-Pyr)$_3$, Nb(=NtBu)(iBu,H,iBu-Pyr)$_3$, Nb(=NtBu)(tAmyl,H,tAmyl-Pyr)$_3$, Nb(=NtBu)(iPr,H,tBu-Pyr)$_3$, Nb(=NtBu)(iPr,H,Me-Pyr)$_3$, Nb(=NtBu)(iPr,H,Et-Pyr)$_3$, Nb(=NtBu)(TMS,H,TMS-Pyr)$_3$, Nb(=NtBu)(DMS,H,DMS-Pyr)$_3$, or Nb(=NtBu)(MMS,H,MMS-Pyr)$_3$.

When R=tAmyl, the Niobium-containing film forming precursor may have the formula Nb(=NtAmyl)($R^1$,$R^2$,$R^3$-Pyr)$_3$:

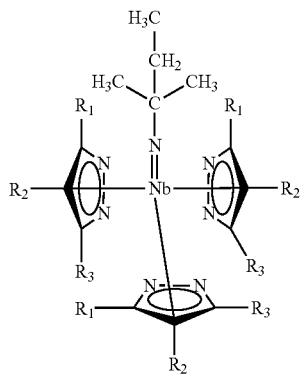

wherein each $R^1$, $R^2$, and $R^3$ is independently H, an alkyl group, or $SiR'_3$, with each R' independently being H or an alkyl group. Preferably, each $R^1$, $R^2$, and $R^3$ is independently H, Me, Et, nPr, iPr, tBu, sBu, iBu, nBu, tAmyl, $SiMe_3$, $SiMe_2H$, or $SiH_2Me$.

Exemplary precursors include Nb(=NtAmyl)(H,H,H-Pyr)$_3$, Nb(=NtAmyl)(Me,H,H-Pyr)$_3$, Nb(=NtAmyl)(Me,H,Me-Pyr)$_3$, Nb(=NtAmyl)(Me,Me,Me-Pyr)$_3$, Nb(=NtAmyl)(Et,H,Et-Pyr)$_3$, Nb(=NtAmyl)(nPr,H,nPr-Pyr)$_3$, Nb(=NtAmyl)(iPr,H,iPr-Pyr)$_3$, Nb(=NtAmyl)(tBu,H,tBu-Pyr)$_3$, Nb(=NtAmyl)(sBu,H,sBu-Pyr)$_3$, Nb(=NtAmyl)(nBu,H,nBu-Pyr)$_3$, Nb(=NtAmyl)(iBu,H,iBu-Pyr)$_3$, Nb(=NtAmyl)(tAmyl,H,tAmyl-Pyr)$_3$, Nb(=NtAmyl)(iPr,H,tBu-Pyr)$_3$, Nb(=NtAmyl)(iPr,H,Me-Pyr)$_3$, Nb(=NtAmyl)(iPr,H,Et-Pyr)$_3$, Nb(=NtAmyl)(TMS,H,TMS-Pyr)$_3$, Nb(=NtAmyl)(DMS,H,DMS-Pyr)$_3$, or Nb(=NtAmyl)(MMS,H,MMS-Pyr)$_3$.

These precursors may be synthesized by reacting Nb(=NR)X$_3$(py)$_2$ with 3 equivalents of Z($R^1$,$R^2$,$R^3$-Pyr) wherein X is an halogen selected from the group consisting of F, Cl, Br and I; Z is an alkali metal selected from the group consisting of Li, Na and K; and R, $R^1$, $R^2$, and $R^3$ is defined above. Nb(=NR)X$_3$(py)$_2$ may be prepared as described in Chemische Berichte, Vol 127, Issue 7, 1994, 1201-12. Z($R^1$,$R^2$,$R^3$-Pyr) may be prepared by reaction of an alkyl alkali-metal, such as n-Butyl Lithium (nBuLi), with the corresponding $R^1$,$R^2$,$R^3$-pyrazole. The additions of the reactants may be done at low temperature, the temperature being below −50° C. The reaction may be done in a polar solvent, such as THF or diethylether. The precursor may be separated from alkali salts by extraction with a non polar solvent, such as pentane, hexane, cyclohexane, heptanes, benzene and toluene. The resulting Niobium-containing film forming composition may be purified by vacuum sublimation, vacuum distillation or by recrystallisation in a suitable solvent selected without limitation from the group consisting of THF, diethylether, pentane, hexane, cyclohexane, heptanes, benzene, toluene, or mixtures thereof.

Purity of the disclosed Niobium-containing film forming composition is greater than 95% w/w (i.e., 95.0% w/w to 100.0% w/w), preferably greater than 98% w/w (i.e., 98.0% w/w to 100.0% w/w), and more preferably greater than 99% w/w (i.e., 99.0% w/w to 100.0% w/w). One of ordinary skill in the art will recognize that the purity may be determined by H NMR or gas or liquid chromatography with mass spectrometry. The disclosed Niobium-containing film forming compositions may contain any of the following impurities: pyrazoles; pyridines; alkylamines; alkylimines; THF; ether; pentane; cyclohexane; heptanes; benzene; toluene; chlorinated metal compounds; or lithium, sodium, or potassium pyrazolyl. The total quantity of these impurities is below 5% w/w (i.e., 0.0% w/w to 5.0% w/w), preferably below 2% w/w (i.e., 0.0% w/w to 2.0% w/w), and more preferably below 1% w/w (i.e. 0.0% w/w to 1.0% w/w). The composition may be purified by recrystallisation, sublimation, distillation, and/or passing the gas or liquid through a suitable adsorbent, such as a 4A molecular sieve.

Purification of the disclosed Niobium-containing film forming composition may also result in metal impurities at the 0 ppbw to 1 ppmw, preferably 0-500 ppbw (part per billion weight) level. These metal impurities include, but are not limited to, Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), and Zinc (Zn).

Also disclosed are methods for forming Niobium-containing layers on a substrate using a vapor deposition process. Applicants believe, and demonstrate in the Deposition Example that follows, that the disclosed Niobium-containing film forming compositions are suitable for atomic layer deposition. More particularly, the disclosed Niobium-containing film forming compositions are capable of surface saturation, self limited growth per cycle, and perfect step coverage on aspects ratios ranging from approximately 2:1 to approximately 200:1, and preferably from approximately 20:1 to approximately 100:1. Additionally, the disclosed Niobium-containing film forming compositions have high decomposition temperatures, indicating good thermal stability to enable ALD. The high decomposition temperatures permit ALD at higher temperatures, resulting in films having higher purity.

The method may be useful in the manufacture of semiconductor, photovoltaic, LCD-TFT, or flat panel type devices. The disclosed Niobium-containing film forming compositions may be used to deposit Niobium-containing films using any deposition methods known to those of skill in the art. Examples of suitable vapor deposition methods include chemical vapor deposition (CVD) or atomic layer deposition (ALD). Exemplary CVD methods include thermal CVD, plasma enhanced CVD (PECVD), pulsed CVD (PCVD), low pressure CVD (LPCVD), sub-atmospheric CVD (SACVD) or atmospheric pressure CVD (APCVD), hot-wire CVD (HWCVD, also known as cat-CVD, in which a hot wire serves as an energy source for the deposition process), radicals incorporated CVD, and combinations thereof. Exemplary ALD methods include thermal ALD, plasma enhanced ALD (PEALD), spatial isolation ALD, hot-wire ALD (HWALD), radicals incorporated ALD, and combinations thereof. Super critical fluid deposition may also be used. The deposition method is preferably ALD, PE-ALD, or spatial ALD in order to provide suitable step coverage and film thickness control.

The disclosed Niobium-containing film forming compositions may be supplied either in neat form or in a blend with a suitable solvent, such as ethyl benzene, xylene, mesitylene, decalin, decane, dodecane. The disclosed precursors may be present in varying concentrations in the solvent.

The neat or blended Niobium-containing film forming compositions are introduced into a reactor in vapor form by conventional means, such as tubing and/or flow meters. The vapor form may be produced by vaporizing the neat or blended composition through a conventional vaporization step such as direct vaporization, distillation, or by bubbling, or by using a sublimator such as the one disclosed in PCX Publication WO2009/087609 to Xu et al. The neat or blended composition may be fed in liquid state to a vaporizer where it is vaporized before it is introduced into the reactor. Alternatively, the neat or blended composition may be vaporized by passing a carrier gas into a container containing the composition or by bubbling the carrier gas into the composition. The carrier gas may include, but is not limited to, Ar, He, $N_2$, and mixtures thereof. Bubbling with a carrier gas may also remove any dissolved oxygen present in the neat or blended composition. The carrier gas and composition are then introduced into the reactor as a vapor.

If necessary, the container containing the disclosed composition may be heated to a temperature that permits the composition to be in its liquid phase and to have a sufficient vapor pressure. The container may be maintained at temperatures in the range of, for example, approximately 0° C. to approximately 180° C. Those skilled in the art recognize that the temperature of the container may be adjusted in a known manner to control the amount of precursor vaporized.

The reactor may be any enclosure or chamber within a device in which deposition methods take place such as without limitation, a parallel-plate type reactor, a cold-wall type reactor, a hot-wall type reactor, a single-wafer reactor, a multi-wafer reactor, or other types of deposition systems under conditions suitable to cause the compounds to react and form the layers. One of ordinary skill in the art will recognize that any of these reactors may be used for either ALD or CVD deposition processes.

The reactor contains one or more substrates onto which the films will be deposited. A substrate is generally defined as the material on which a process is conducted. The substrates may be any suitable substrate used in semiconductor, photovoltaic, fiat panel, or LCD-TFT device manufacturing. Examples of suitable substrates include wafers, such as silicon, silica, glass, or GaAs wafers. The wafer may have one or more layers of differing materials deposited on it from a previous manufacturing step. For example, the wafers may include silicon layers (crystalline, amorphous, porous, etc.), silicon oxide layers, silicon nitride layers, silicon oxy nitride layers, carbon doped silicon oxide (Si-COH) layers, metal or metal nitride layers (Ti, Ru, Ta, etc.) or combinations thereof. Additionally, the wafers may include copper layers or noble metal layers (e.g. platinum, palladium, rhodium, or gold). The wafers may include barrier layers, such as manganese, manganese oxide, etc. Plastic layers, such as poly(3,4-ethylenedioxythiophene) poly(styrenesulfonate)[PEDOT:PSS] may also be used. The layers may be planar or patterned. The disclosed processes may deposit the Niobium-containing layer directly on the wafer or directly on one or more than one (when patterned layers form the substrate) of the layers on top of the wafer. Furthermore, one of ordinary skill in the art will recognize that the terms "film" or "layer" used herein refer to a thickness of some material laid on or spread over a surface and that the surface may be a trench or a line. Throughout the specification and claims, the wafer and any associated layers thereon are referred to as substrates. For example, a Niobium oxide film may be deposited onto a metal oxide layer, such as a $ZrO_2$ layer, an $HfO_2$ layer, or an $MoO_2$ layer. In subsequent processing, another metal oxide layer may be deposited on the Niobium oxide layer to form a laminate. $ZrO_2/Nb_2O_5/ZrO_2$ laminate dielectric stack are typical of DRAM high-k stack. A conductive metal nitride layer, such as a Niobium Nitride layer or a Titanium nitride layer, may be deposited before or on the last metal oxide layer to form, respectively, the bottom and top electrodes. The resulting $NbN/ZrO_2O_5/ZrO_2/NbN$ stack may be used in DRAM capacitors. Other conductive films, such as RuO, Ru, Pt, Ir, WN, WNC, may be also used as the bottom or top electrodes, alone or in addition to the NbN or TaN layers.

The temperature and the pressure within the reactor are held at conditions suitable for Atomic Layer Deposition. In other words, after introduction of the vaporized composition into the chamber, conditions within the chamber are such that at least part of the precursor is deposited onto the substrate to form a Niobium-containing layer. For instance, the pressure in the reactor may be held between about 1 Pa and about $10^5$ Pa, more preferably between about 25 Pa and about $10^3$ Pa, as required per the deposition parameters. Likewise, the temperature in the reactor may be held between about 100° C. and about 500° C, preferably between about 150° C. and about 400°G. One of ordinary skill in the art will recognize that "at least part of the precursor is deposited" means that some or all of the precursor reacts with or adheres to the substrate.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 100° C. to approximately 500° C. When a plasma deposition process is utilized, the deposition temperature may range from approximately 150° C. to approximately 400° C. Alternatively, when a thermal process is performed, the deposition temperature may range from approximately 200° C. to approximately 500° C.

In addition to the disclosed Niobium-containing film forming composition, a reactant may be introduced into the reactor. When the target is a conductive film, the reactant may be $H_2$, $H_2CO$, $N_2H_4$, $NH_3$, a primary amine, a secondary amine, a tertiary amine, trisilylamine, radicals thereof, and mixtures thereof. Preferably, the reactant is $H_2$ or $NH_3$.

Alternatively, when the target is a dielectric film, the reactant may be an oxidizing gas such as one of $O_2$, $O_3$, $H_2O$, $H_2O_2$, NO, $N_2O$, $NO_2$, oxygen containing radicals such as O— or OH—, carboxylic acids, formic acid, acetic acid, propionic acid, and mixtures thereof. Preferably, the oxidizing gas is selected from the group consisting of $O_3$, $H_2O_2$ or $H_2O$.

The reactant may be treated by a plasma, in order to decompose the reactant into its radical form. $N_2$ may also be utilized as a nitrogen source gas when treated with plasma. For instance, the plasma may be generated with a power ranging from about 50 W to about 500 W, preferably from about 100 W to about 400 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

For example, the reactant may be introduced into a direct plasma reactor, which generates plasma in the reaction chamber, to produce the plasma-treated reactant in the reaction chamber. Exemplary direct plasma reactors include the Titan™ PECVD System produced by Trion Technologies. The reactant may be introduced and held in the reaction chamber prior to plasma processing. Alternatively, the plasma processing may occur simultaneously with the introduction of the reactant. In-situ plasma is typically a 13.56 MHz RF inductively coupled plasma that is generated between the showerhead and the substrate holder. The substrate or the showerhead may be the powered electrode depending on whether positive ion impact occurs. Typical applied powers in in-situ plasma generators are from approximately 30 W to approximately 1000 W. Preferably, powers from approximately 30 W to approximately 600 W are used in the disclosed methods. More preferably, the powers range from approximately 100 W to approximately 500 W. The disassociation of the reactant using in-situ plasma is typically less than achieved using a remote plasma source for the same power input and is therefore not as efficient in reactant dissociation as a remote plasma system, which may be beneficial for the deposition of Niobium-containing films on substrates easily damaged by plasma.

Alternatively, the plasma-treated reactant may be produced outside of the reaction chamber. The MKS Instruments' ASTRONi® reactive gas generator may be used to treat the reactant prior to passage into the reaction chamber. Operated at 2.45 GHz, 7kW plasma power, and a pressure ranging from approximately 0.5 Torr to approximately 10 Torr, the reactant $O_2$ may be decomposed into two O' radicals. Preferably, the remote plasma may be generated with a power ranging from about 1 kW to about 10 kW, more preferably from about 2.5 kW to about 7.5 kW.

The Atomic Layer deposition conditions within the chamber allow the disclosed Nb composition adsorbed or chemisorbed on the substrate surface to react and form a Niobium-containing film on the substrate. In some embodiments, Applicants believe that plasma-treating the reactant may provide the reactant with the energy needed to react with the disclosed composition.

Depending on what type of film is desired to be deposited, an additional precursor compound may be introduced into the reactor. The precursor may be used to provide additional elements to the Niobium-containing film. The additional elements may include lanthanides (Ytterbium, Erbium, Dysprosium, Gadolinium, Praseodymium, Cerium, Lanthanum, Yttrium), Group IV elements (zirconium, titanium, hafnium), main group elements (germanium, silicon, aluminium), additional Group V elements (Tantalum, Vanadium), or mixtures of these. When an additional precursor compound is utilized, the resultant film deposited on the substrate contains the Niobium metal in combination with an additional element. When the additional precursor and the Nb precursors are used in more than one ALD super cycle sequences, a nanolaminate film is obtained.

The Niobium-containing film forming composition and reactants may be introduced into the reactor sequentially (atomic layer deposition). The reactor may be purged with an inert gas between the introduction of each of the Nb-containing film forming composition, any additional precursors, and the reactants. Another example is to introduce the reactant continuously and to introduce the Niobium-containing film forming composition by pulse, while activating the reactant sequentially with a plasma, provided that the Nb composition and the non-activated reactant do not substantially react at the chamber temperature and pressure conditions (CW PEALD).

Each pulse of composition may last for a time period ranging from about 0.01 seconds to about 120 seconds, alternatively from about 1 seconds to about 80 seconds, alternatively from about 5 seconds to about 30 seconds. The reactant may also be pulsed into the reactor. In such embodiments, the pulse of each may last for a time period ranging from about 0.01 seconds to about 120 seconds, alternatively from about 1 seconds to about 30 seconds, alternatively from about 2 seconds to about 20 seconds. In another alternative, the vaporized compositions and reactants may be simultaneously sprayed from different sectors of a shower head (without mixing of the composition and the reactant) under which a susceptor holding several wafers is spun (spatial ALD).

Depending on the particular process parameters, deposition may take place for a varying length of time. Generally, deposition may be allowed to continue as long as desired or necessary to produce a film with the necessary properties. Typical film thicknesses may vary from several angstroms to several hundreds of microns, and typically from 2 to 100 nm, depending on the specific deposition process. The deposition process may also be performed as many times as necessary to obtain the desired film.

In one non-limiting exemplary ALD process, the vapor phase of the disclosed Niobium-containing film forming composition is introduced into the reactor, where it is contacted with a suitable substrate. Excess composition may then be removed from the reactor by purging and/or evacuating the reactor. A reactant (for example, $NH_3$) is introduced into the reactor where it reacts with the absorbed composition in a self-limiting manner. Any excess reactant is removed from the reactor by purging and/or evacuating the reactor. If the desired film is a Niobium Nitride, this two-step process may provide the desired film thickness or may be repeated until a film having the necessary thickness has been obtained.

Alternatively, if the desired film contains the Niobium transition metal and a second element, the two-step process above may be followed by introduction of the vapor of an additional precursor compound into the reactor. The additional precursor compound will be selected based on the nature of the Niobium-containing film being deposited. After introduction into the reactor, the additional precursor compound is contacted with the substrate. Any excess precursor compound is removed from the reactor by purging and/or evacuating the reactor. Once again, a reactant may be introduced into the reactor to react with the precursor compound. Excess reactant is removed from the reactor by purging and/or evacuating the reactor. If a desired film thickness has been achieved, the process may be terminated. However, if a thicker film is desired, the entire four-step process may be repeated. By alternating the provision of the Niobium-containing film forming composition, additional precursor compound, and reactant, a film of desired composition and thickness can be deposited.

When the reactant in this exemplary ALD process is treated with a plasma, the exemplary ALD process becomes an exemplary PEALD process. The reactant may be treated with plasma prior or subsequent to introduction into the chamber.

In a second non-limiting exemplary ALD process, the vapor phase of one of the disclosed Niobium-containing film forming composition, for example Niobium (tbutyl imido) tris(3,5-diisopropylpyrazolyl) (Nb(=NtBu)(iPr,H,iPr-Pyr)$_3$), is introduced into the reactor, where it is contacted with a Si substrate. Excess composition may then be removed from the reactor by purging and/or evacuating the reactor. A reactant (for example, $NH_3$) is introduced into the reactor where it reacts with the absorbed composition in a self-limiting manner to form a Niobium Nitride film. Any excess $NH_3$ gas is removed from the reactor by purging and/or evacuating the reactor. These two steps may be repeated until the Niobium Nitride film obtains a desired thickness, typically around 10 angstroms. $ZrO_2$ may then be deposited on the NbN film. For example, $ZrCp(NMe_2)_3$ may serve as the Zr precursor. The second non-limiting exemplary ALD process described above using Nb(=NtBu)(iPr,H,iPr-Pyr)$_3$ and $NH_3$ may then be repeated on the $ZrO_2$ layer. The resulting NbN/$ZrO_2$/NbN stack may be used in DRAM capacitors.

In another exemplary ALD process, another precursor may be introduced sequentially between one or several ALD super-cycles (e.g., O-containing reactant/Nb precursor/O-containing reactant) in order to deposit a NbMO film or an NbO/MO nanolaminate, M being selected from a Group IV element, a different group V element, silicon, germanium, aluminium, or any lanthanide. The M precursor selected preferably undergoes ALD growth in the same temperature window exhibited by the selected Nb-containing film forming composition.

The Niobium-containing films resulting from the processes discussed above may include Nb, $Nb_kSi_l$, $Nb_nO_m$, $Nb_oN_p$, or $Nb_oN_pO_q$, wherein k, l, m, n, o, p, and q may each independently range from 1 to 6. Exemplary films include $NbO_2$, $Nb_2O_5$, NbN, and NbON. One of ordinary skill in the art will recognize that by judicial selection of the appropriate niobium-containing film forming composition reactants, the desired film composition may be obtained. The NbN films may provide suitable step coverage for capacitor electrodes in DRAM, the gate metal in 3D Flash memory devices, the heating element in phase change memory, or the electromigration barrier layer, gate metal, and contact layers in logic devices.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the NbN film may be exposed to a temperature ranging from approximately 200° C. and approximately 1000° C. for a time ranging from approximately 0.1 second to approximately 7200 seconds under an inert atmosphere, a N-containing atmosphere, or combinations thereof. Most preferably, the temperature is 400° C. for 3600 seconds under an inert atmosphere or a N-containing atmosphere. The resulting film may contain fewer impurities and therefore may have an improved density resulting in improved leakage current. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the NbN film. This in turn tends to improve the resistivity of the film.

After annealing, the NbN films deposited by any of the disclosed processes may have a bulk resistivity at room temperature of approximately 50 μohm.cm to approximately 1,000 μohm.cm. Room temperature is approximately 20° C. to approximately 28° C. depending on the season. Bulk resistivity is also known as volume resistivity. One of ordinary skill in the art will recognize that the bulk resistivity is measured at room temperature on NbN films that are typically approximately 50 nm thick. The bulk resistivity typically increases for thinner films due to changes in the electron transport mechanism. The bulk resistivity also increases at higher temperatures.

In another alternative, the disclosed compositions may be used as doping or implantation agents. Part of the disclosed composition may be deposited on top of the film to be doped, such as an indium oxide ($In_2O_3$) film, tantalum dioxide ($TaO_2$), vanadium dioxide ($VO_2$) film, a titanium oxide film, a copper oxide film, or a tin dioxide ($SnO_2$) film. The Niobium then diffuses into the film during an annealing step to form the Niobium-doped films {(Nb)$In_2O_3$, (Nb)$VO_2$, (Nb)TiO, (Nb)CuO, (Nb)$SnO_2$}. See, e.g., US2008/0241575 to Lavoie et al., the doping method of which is incorporated herein by reference in its entirety.

EXAMPLES

The following non-limiting examples are provided to further illustrate embodiments of the invention. However, the examples are not intended to be all inclusive and are not intended to limit the scope of the inventions described herein.

Example 1

Synthesis of Niobium (tButylimido) tris(3,5-dimethylpyrazolyl)

To a solution of 1H-3,5-dimethylpyrazole (2 g, 0.00214 mol) in 40 ml of THF at −78° C., was added dropwise nBuli (14 mL, 1.6M). After stirring 1 night at room temperature, the mixture was added to a solution of Nb(=NtBu)Cl3(py)$_2$ (3 g, 0.00678 mmol) in 500 ml of THF at −78° C. The mixture was stirred overnight at room temperature. Solvent was then removed under vacuum and the product was extracted with pentane to give a yellow solid. The material was then purified by sublimation up to 130° C. @25 mTorr to give 0.64 g (20%) of pure yellow solid. The NMR $^1$H spectrum is provided in FIG. 1. NMR$^1$H (δ, ppm, C6D6): 6.04 (s, 3H), 2.31(s, 18H), 0.96 (s, 9H).

Figure 2:
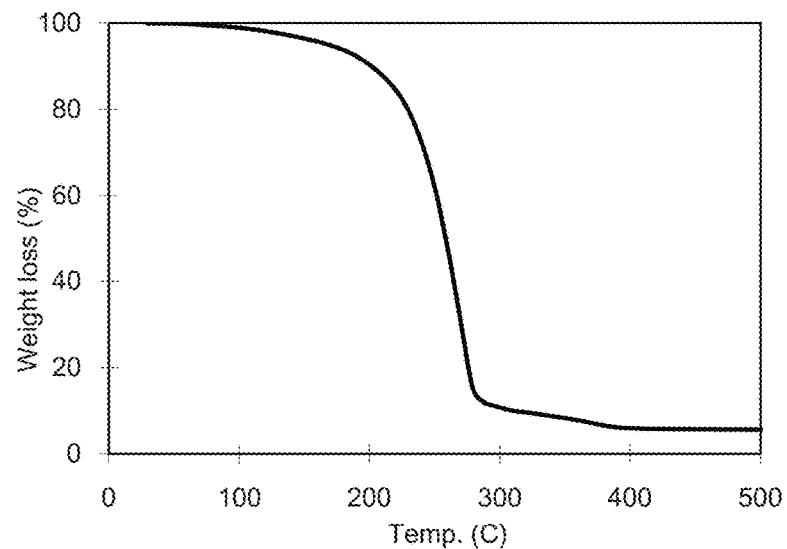
FIG. 2 is a ThermoGravimetric Analysis (TGA) graph demonstrating the percentage of weight loss with increasing temperature of Nb(=NtBu)(Me,H,Me-Pyr)$_3$.
Figure 3:
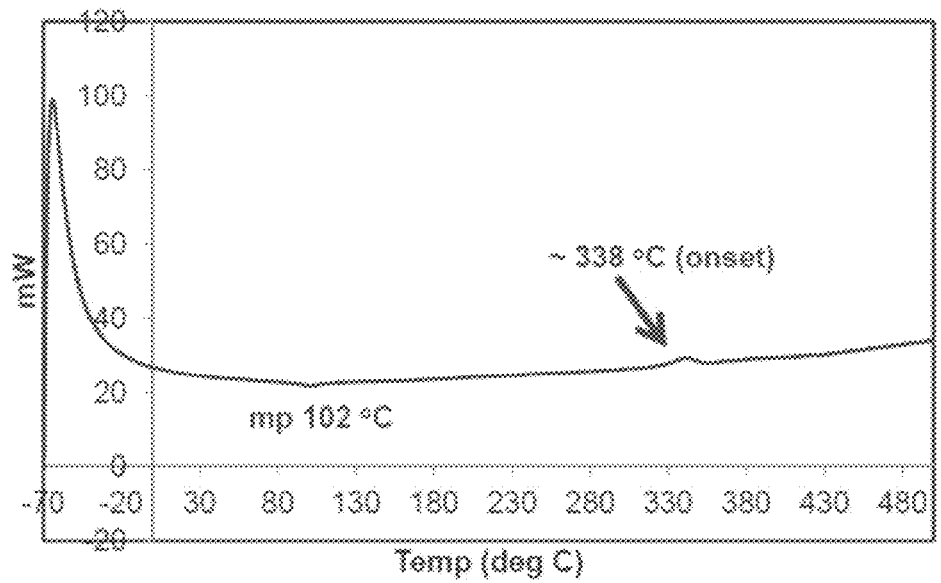
FIG. 3 is a Differential Scanning Calorimetry (DSC) graph demonstrating the melting point and decomposition temperature of Nb(=NtBu)(Me,H,Me-Pyr)$_3$.

The solid left a 5.6% residual mass during Open-Cup TGA analysis measured at a temperature rising rate of 10° C./min in an atmosphere which flows nitrogen at 200 mL/min (15% during Close-Cup). These results are shown in FIG. 2, which is a TGA graph illustrating the percentage of weight loss upon temperature increase. As shown in FIG. 3, the melting point was determined using Differential Scanning Calorimetry (DSC) to be approximately 95° C. FIG. 3 also discloses that the temperature at which decomposition commences is 338° C., indicating a good thermal stability to enable ALD (no self decomposition on the wafer surface).

Example 2

Synthesis of Niobium (tAmylimido) tris(3,5-dimethylpyrazolyl)

Figure 4:
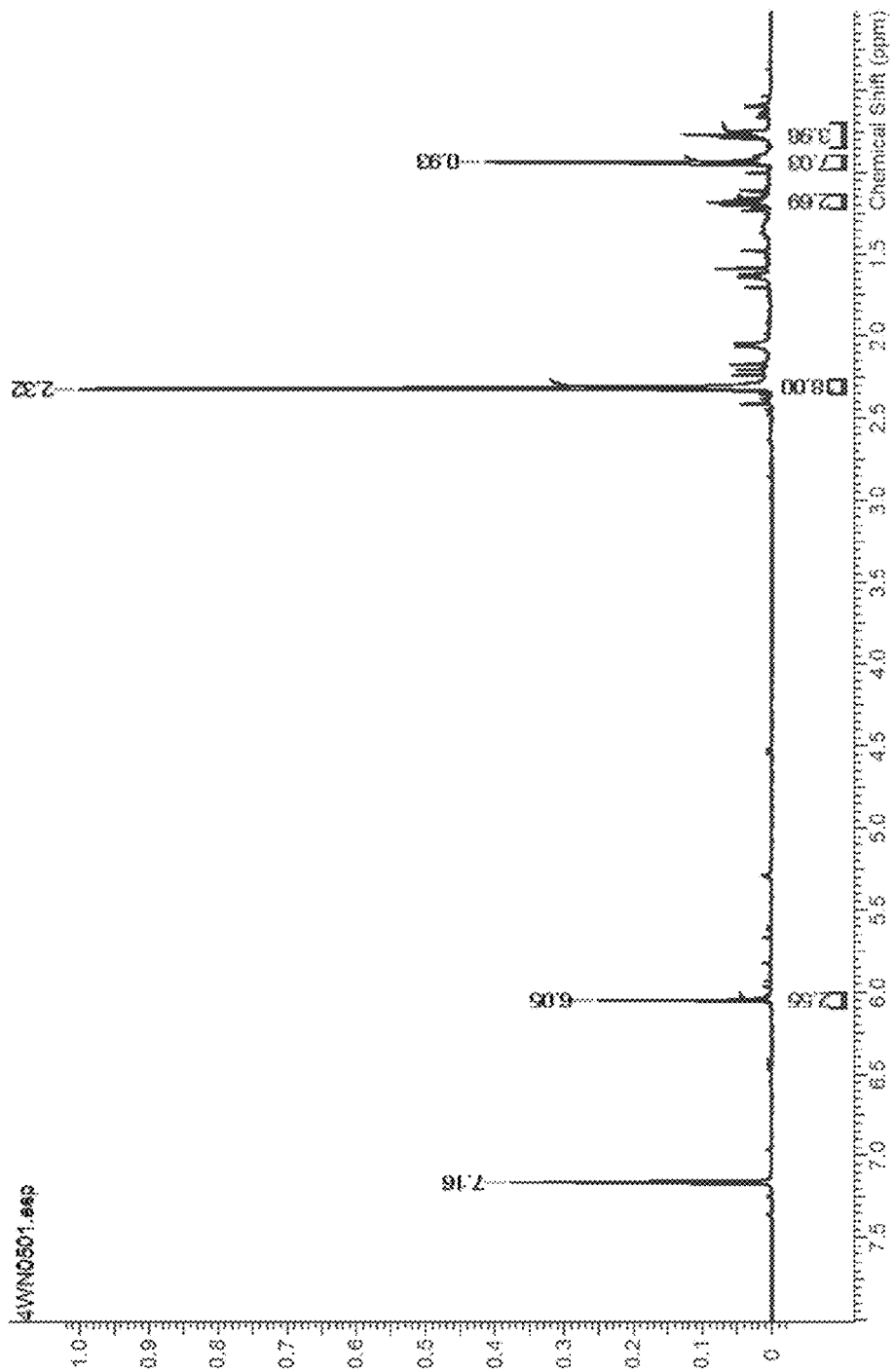
FIG. 4 is a $^1$HNMR spectrum of Niobium (tAmylimido) tris(3,5-dimethylpyrazolyl) [Nb(=NtAm)(Me,H,Me-Pyr)$_3$]

To a solution of 1H-3,5-dimethylpyrazole (2 g, 20.81 mmol) in 40 ml of THF at −78° C., was added dropwise nBuli (14 ml, 1.6 M). After stirring for 6 hrs at room temperature, the mixture was added to a solution of Nb(=NtAmyl)Cl$_3$(py)$_2$ (3 g, 8.78 mmol) in 30 ml of THF at −78° C. The mixture was stirred overnight at room temperature. Solvent was then removed under vacuum and the product was extracted with pentane to give a yellow solid. The material was then purified by sublimation up to 130° C. @25 mTorr to give 0.64 g (20%) of pure yellow solid. The NMR $^1$H spectrum is provided in FIG. 4. NMR$^1$H (δ, ppm, C6D6): 6.05 (s, 3H), 2.32 (s, 18H), 1.18 (q, 2H), 0.93 (s, 6H), 0.77 (t, 3H).

Figure 5:
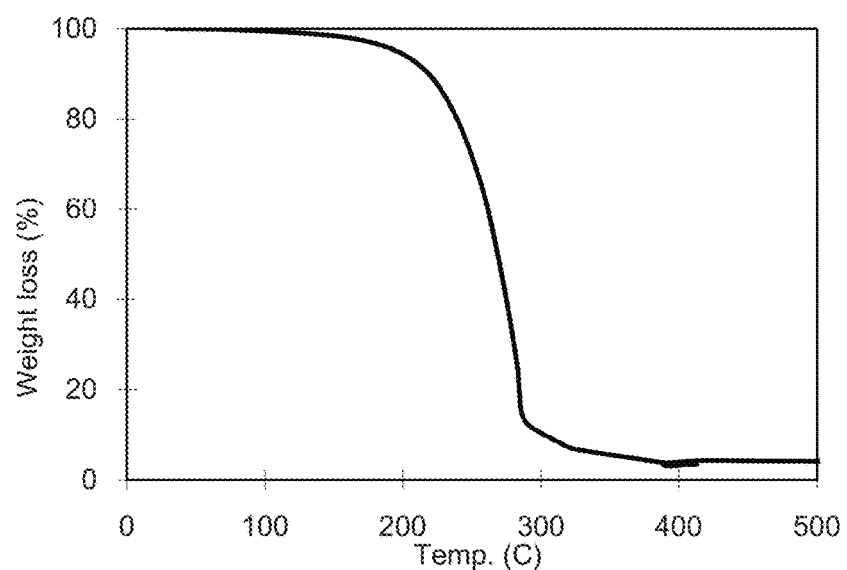
FIG. 5 is a TGA graph demonstrating the percentage of weight loss with increasing temperature of Nb(=NtAm)(Me,H,Me-Pyr)$_3$.

The solid left a 4.1% residual mass during Open-Cup TGA analysis measured at a temperature rising rate of 10° C/min in an atmosphere which flows nitrogen at 200 mL/min (15% during Close-Cup). These results are shown in FIG. 5, which is a TGA graph illustrating the percentage of weight loss upon temperature increase. Melting point was determined using DSC to be approximately 96° C., which illustrates that use of the tAmyl group did not help reduce the melting point.

Example 3

Synthesis of Niobium (tButylimido) tris(3-methylpyrazolyl)

To a solution of 1H-3-methylpyrazole (1.8 g, 21.92 mmol) in 50 ml of THF at room temperature, were added freshly cut pieces of potassium (0.94 g, 24.04 mmol). After stirring 6 hrs at room temperature, the mixture was added to a solution of Nb(=NtBu)Cl$_3$(py)$_2$ (3 g, 7.00 mmol) in 40 ml of THF at −78 ° C. The mixture was stirred overnight at room temperature. Solvent was then removed under vacuum and the product was extracted with pentane to give yellow solid. The material was then subject to sublimation up to 170 ° C. @20 mTorr, but the color changed to black and no material was collected.

Alternatively, to a solution of 1H-3-methylpyrazole (1.8 g, 21.92 mmol) in 50 ml of THF at −78 ° C, was added dropwise nBuli (14 ml, 1.6 M). After stirring 6 hrs at room temperature, the mixture was added to a solution of Nb(=NtBu)Cl$_3$(py)$_2$ (3 g, 7.00 mmol) in 40 ml of THF at −78 ° C. The mixture was stirred overnight at room temperature. Solvent was then removed under vacuum and the product was extracted with pentane to give orange solid. The material was then subject to sublimation up to 150° C. @50 mTorr, but the color changed to dark brown and no material was collected.

Example 4

Synthesis of Niobium (tButylimido) tris(3,5-diisopropylpyrazolyl)

Figure 6:
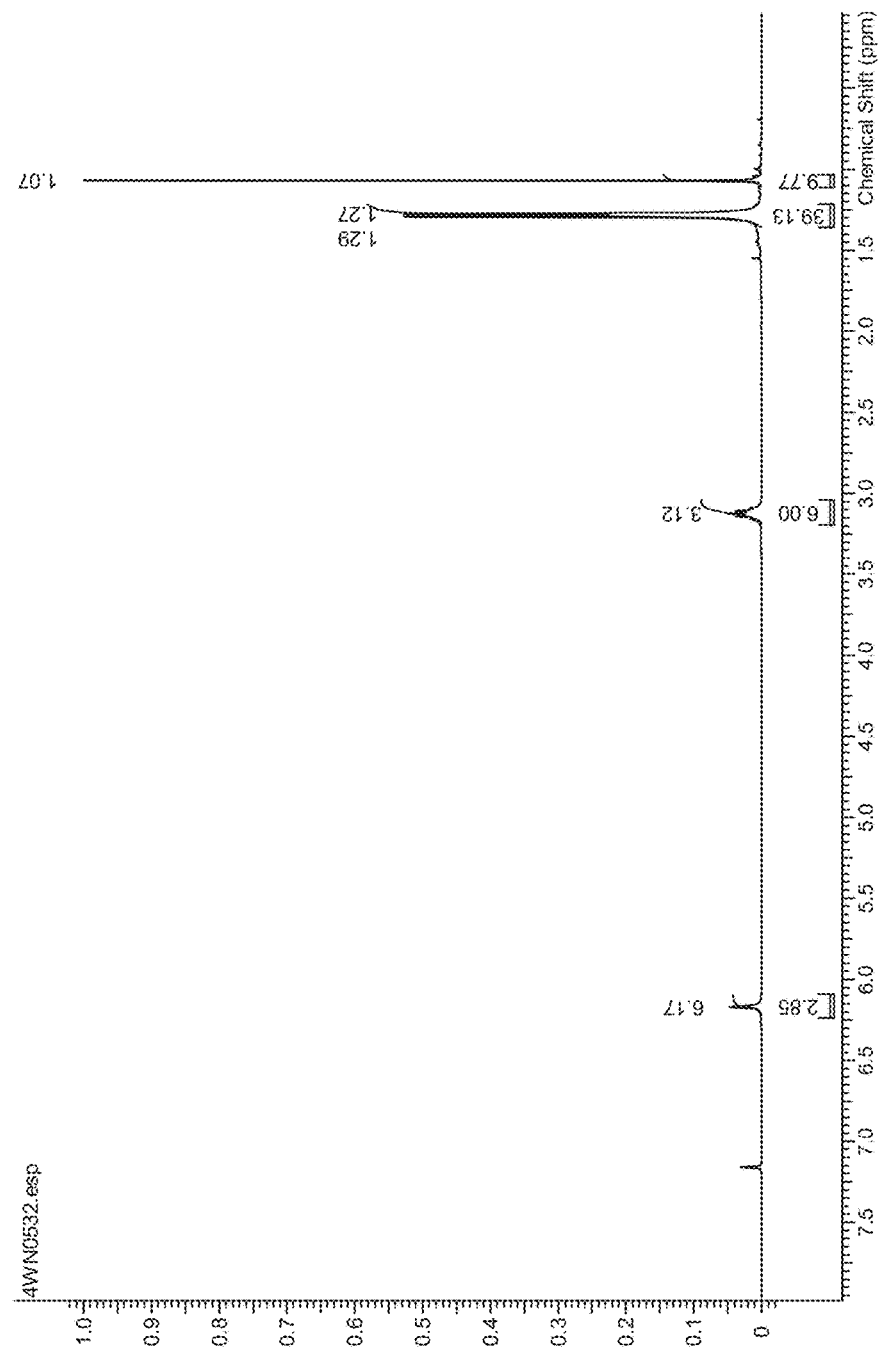
FIG. 6 is a $^1$HNMR spectrum of Niobium (tButylimido) tris(3,5-diisopropylpyrazolyl) [Nb(=NtBu)(iPr,H,iPr-Pyr)$_3$]

To a solution of 1H-3,5-diisopropylpyrazole (73 g, 0.48 mol) in 800 ml of THF at −78° C, was added dropwise nBuli (195 mL, 2.5M). After stirring 1 night at room temperature, the mixture was added to a solution of Nb(=NtBu)Cl$_3$(py)$_2$ (66 g, 0.154 mmol) in 500 ml of THF at −78° C. The mixture was stirred overnight at room temperature. Solvent was then removed under vacuum and the product was extracted with pentane to give a yellow oil. The material was then purified by distillation up to 220° C. @20 mTorr to give 72 g (76%) of pure yellow oil. The NMR $^1$H spectrum is provided in FIG. 6. NMR$^1$H (δ, ppm, C6D6): 6.17 (s, 3H), 3.12 (m, 6H), 1.27 (d, 36H), 1.07 (s, 9H).

Figure 7:
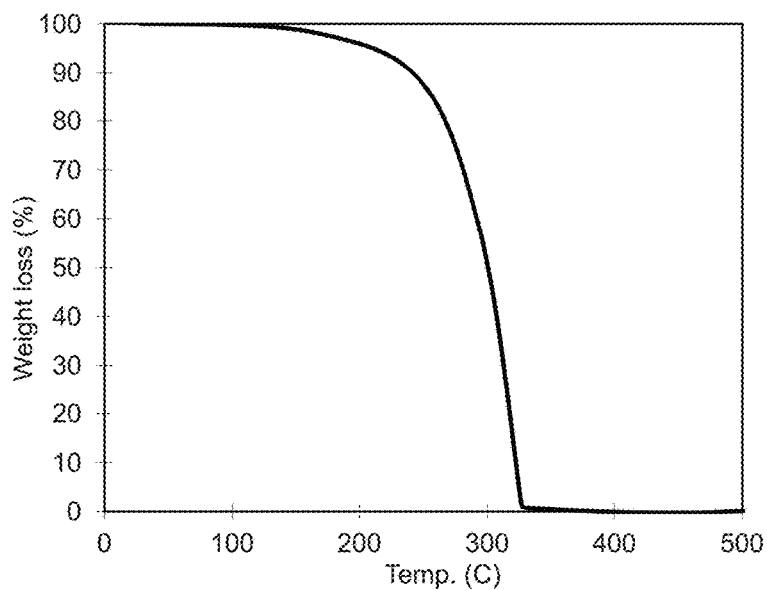
FIG. 7 is a TGA graph demonstrating the percentage of weight loss with increasing temperature of Nb(=NtBu)(iPr,H,iPr-Pyr)$_3$.
Figure 8:
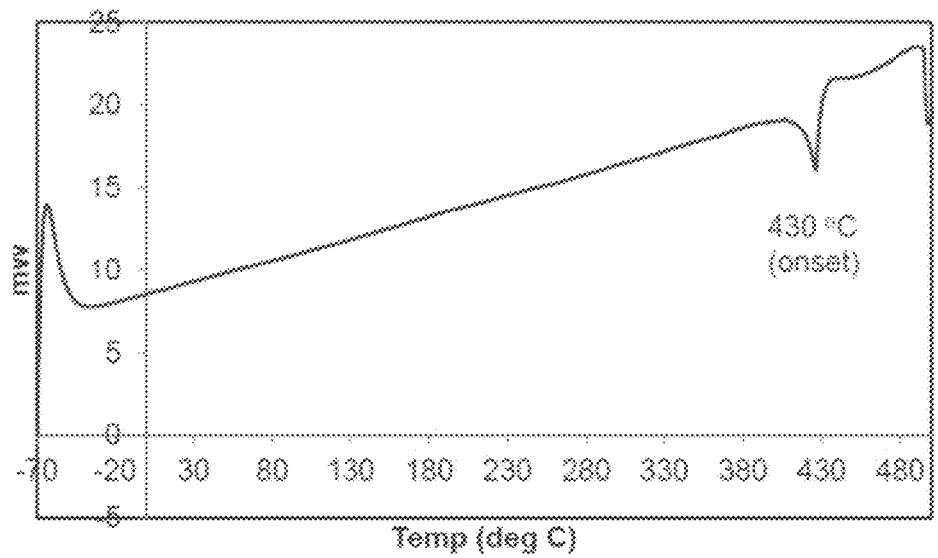
FIG. 8 is a DSC graph demonstrating the melting point and decomposition temperature of Nb(=NtBu)(iPr,H,iPr-Pyr)$_3$.

The oil left a 1.7% residual mass during Open-Cup TGA analysis measured at a temperature rising rate of 10° C./min in an atmosphere which flows nitrogen at 200 ml/min (15% during Close-Cup). These results are shown in FIG. 7, which is a TGA graph illustrating the percentage of weight loss upon temperature increase. As shown in FIG. 8, the decomposition temperature was determined using DSC to commence at approximately 430° C, indicating a good thermal stability to enable ALD (no self decomposition on the wafer surface)

Figure 9:
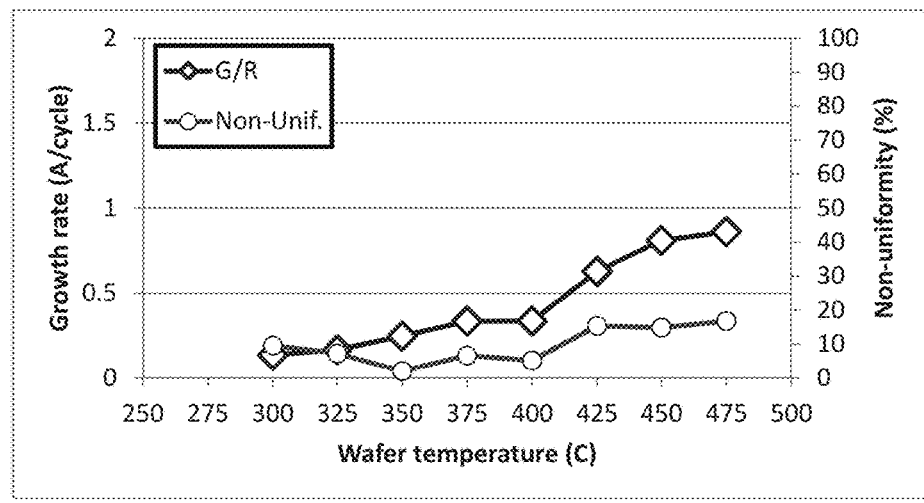
FIG. 9 is a graph showing the niobium nitride film growth rate and % non-uniformity as a function of the chamber temperature using Nb(=NtBu)(iPr,H,iPr-Pyr)$_3$.
Figure 10:
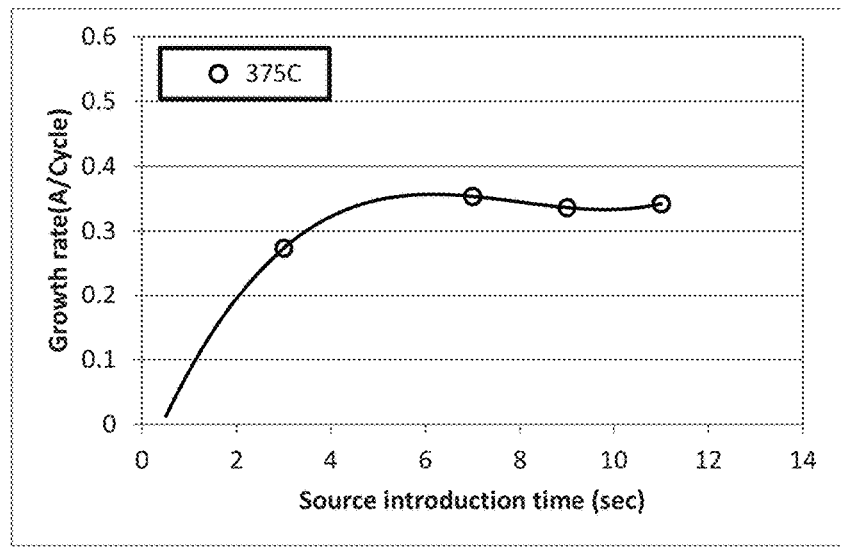
FIG. 10 is a graph showing the niobium nitride film growth rate at 375° C. as a function of precursor source introduction time using Nb(=NtBu)(iPr,H,iPr-Pyr)$_3$.
Figure 11:
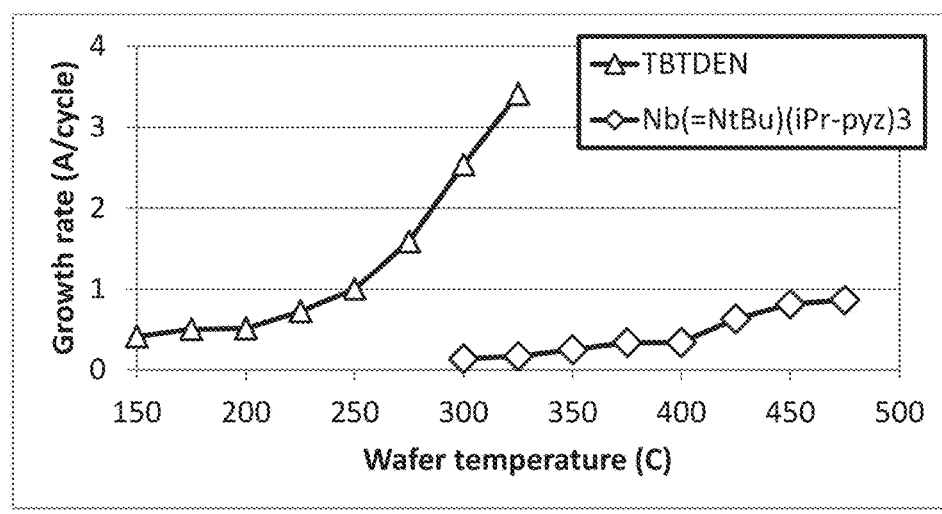
FIG. 11 is a graph showing the niobium nitride film growth rate as a function of the chamber temperature using per number of ALD cycles using Nb(=NtBu)(NEt$_2$)$_3$ and Nb(=NtBu)(iPr,H,iPr-Pyr)$_3$.

The liquid state of this precursor is surprising. Gust et al. report that Nb(=NtBu)(tBu,H,tBu-Pyr)₃ is a white solid (Polyhedron 20 (2001) 805-813 at 808-807). Example 1 demonstrates that the analogous Me product is also a solid (i.e., Nb(=NtBu)(Me,H,Me-Pyr)₃). One of ordinary skill in the art would not expect the iPr substituents to yield a product with properties different from those of its Me or tBu analogs. The unexpected liquid state of this precursor may make vapor delivery of this precursor easier than the solid state of the analogous precursor of Gust et al. and Example 1. More particularly, the liquid state may provide a more consistent and reproducible vapor concentration as compared to that of the solid state precursors. Additionally, the DSC analysis shows a surprisingly high onset of thermal decomposition (430° C.), that makes the compound highly suitable for ALD at elevated temperature (>300° C.), Deposition Example ALD deposition using Nb(=NtBu)(iPr,H,iPr-Pyr)₃ and NH₃ was performed on Si substrates. The canister of Nb(=NtBu)(iPr,H,iPr-Pyr)₃ was maintained at 140° C. The chamber pressure was set at 0.5 torr. The process temperature was set at temperatures ranging from approximately 300° C. to approximately 475° C. These results are shown in FIG. 9, which is a graph showing the NbN film growth rate as a function of the chamber temperature using Nb(=NtBu)(iPr,H,iPr-Pyr)₃. ALD deposition occurred at temperatures ranging from approximately 350° C. to approximately 400° C., where non-uniformity is low. FIG. 10 shows the NbN film growth rate at 375° C. remains stable at ~0.34 A/Cy as the precursor source introduction time is increasing. FIG. 11 is a graph showing the NbN film growth rate as a function of the chamber temperature using Nb(=NtBu)(NEt₂)₃ and Nb(=NtBu)(iPr,H,iPr-Pyr)₃. As shown in FIG. 9, the NbN films from Nb(=NtBu)(iPr,H,iPr-Pyr)₃ are deposited at temperatures approximately 200° C. higher than those from Nb(=NtBu)(NEt₂)₃.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:

1. An atomic layer deposition method of forming a Niobium-containing film, the method comprising introducing into a reactor having a substrate therein a vapor of a Niobium-containing film forming composition comprising a precursor having the formula

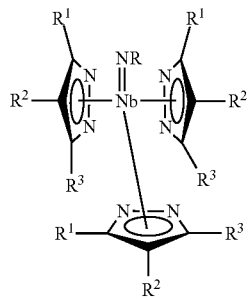

wherein R=tBu, each R²=H, and each R¹ and each R³=iPr; and depositing at least part of the precursor onto the substrate;
introducing a reactant into the reactor;
temporally or spatially introducing an inert gas purge to separate the introduction of the Niobium-containing film forming composition and the introduction of the reactant.

2. The method of claim 1, wherein the reactant is selected from the group consisting of O₂, O₃, H₂O, H₂O₂, NO, N₂O, NO₂, oxygen radicals thereof, and mixtures thereof.

3. The method of claim 1, wherein the substrate is a dielectric layer.

4. The method of claim 2, wherein the reactant is O₃.

5. The method of claim 4, wherein the substrate is a Ru layer.

6. the method of claim 4, wherein the substrate has an aspect ratio ranging from approximately 2:1 to approximately 200:1.

* * * * *